(12) United States Patent
Komatsubara

(10) Patent No.: US 11,677,886 B2
(45) Date of Patent: Jun. 13, 2023

(54) INFORMATION PROCESSING APPARATUS AND NON-TRANSITORY COMPUTER READABLE MEDIUM FOR DETERMINING A PREFERENTIAL USER TERMINAL TO CONNECT WITH

(71) Applicant: FUJIFILM BUSINESS INNOVATION CORP., Tokyo (JP)

(72) Inventor: Keisuke Komatsubara, Kanagawa (JP)

(73) Assignee: FUJIFILM Business Innovation Corp., Tokyo (JP)

(*) Notice: Subject to any disclaimer, the term of this patent is extended or adjusted under 35 U.S.C. 154(b) by 738 days.

(21) Appl. No.: 16/592,848

(22) Filed: Oct. 4, 2019

(65) Prior Publication Data

US 2020/0382673 A1 Dec. 3, 2020

(30) Foreign Application Priority Data

May 27, 2019 (JP) .............................. JP2019-098568

(51) Int. Cl.
*H04N 1/00* (2006.01)
*A61B 5/00* (2006.01)
*A61B 5/024* (2006.01)
*H04N 1/327* (2006.01)

(52) U.S. Cl.
CPC ......... *H04N 1/00923* (2013.01); *A61B 5/024* (2013.01); *A61B 5/681* (2013.01); *H04N 1/00323* (2013.01); *H04N 1/32771* (2013.01)

(58) Field of Classification Search
CPC ............................................... H04N 1/00923
See application file for complete search history.

(56) References Cited

U.S. PATENT DOCUMENTS

| 10,566,082 | B1* | 2/2020 | McNair | ................. | G06Q 50/22 |
| 2006/0251060 | A1* | 11/2006 | Iwakawa | ............. | H04L 65/1101 |
| | | | | | 370/360 |
| 2014/0085652 | A1* | 3/2014 | Yoshida | ............... | H04N 1/4433 |
| | | | | | 358/1.13 |
| 2017/0315482 | A1* | 11/2017 | Tsu | ....................... | G03G 15/205 |

(Continued)

FOREIGN PATENT DOCUMENTS

| JP | 2016-92740 A | 5/2016 |
| JP | 2017-216548 A | 12/2017 |
| JP | 2018-36736 A | 3/2018 |

OTHER PUBLICATIONS

Dec. 6, 2022 Office Action issued in Japanese Patent Application No. 2019-098568.

*Primary Examiner* — Benjamin O Dulaney
(74) *Attorney, Agent, or Firm* — Oliff PLC

(57) ABSTRACT

An information processing apparatus includes a communication unit, an information acquiring unit, a setting unit, and a controller. The communication unit communicatively connects with a terminal device having a sensor. The information acquiring unit acquires information detected by the sensor from the terminal device communicatively connected via the communication unit. The setting unit sets a preferential terminal device to be preferentially connected with the communication unit. The controller performs control to connect with the preferential terminal device preferentially over a terminal device that is not a preferential terminal device within a capacity range of the communication unit.

8 Claims, 8 Drawing Sheets

(56) References Cited

U.S. PATENT DOCUMENTS

| | | | |
|---|---|---|---|
| 2018/0063343 A1 | 3/2018 | Nakata et al. | |
| 2018/0165047 A1* | 6/2018 | Nishio | G06F 3/1211 |
| 2020/0382673 A1* | 12/2020 | Komatsubara | A61B 5/002 |
| 2021/0011443 A1* | 1/2021 | McNamara | F24F 11/0001 |
| 2021/0176617 A1* | 6/2021 | Han | H04W 52/028 |

* cited by examiner

INFORMATION PROCESSING APPARATUS AND NON-TRANSITORY COMPUTER READABLE MEDIUM FOR DETERMINING A PREFERENTIAL USER TERMINAL TO CONNECT WITH

CROSS-REFERENCE TO RELATED APPLICATIONS

This application is based on and claims priority under 35 USC 119 from Japanese Patent Application No. 2019-098568 filed May 27, 2019.

BACKGROUND

(i) Technical Field

The present disclosure relates to information processing apparatuses and non-transitory computer readable media.

(ii) Related Art

An image forming apparatus disclosed in Japanese Unexamined Patent Application Publication No. 2018-036736 includes an image forming unit that forms an image, a display unit that displays information, a communication unit that communicates with sensors as target devices to be managed, a condition ascertaining unit that determines the operating state of each sensor based on the communication with the sensor, and a notification unit that outputs, via the display unit, information related to a sensor whose operating state is determined to be abnormal by the condition ascertaining unit.

Known terminal devices called Internet-of-Things (IoT) devices acquire health-related information of employees working in offices and environment-related information such as temperatures and noise detected by sensors installed in offices. In order to collect and manage the information acquired by such terminal devices, information processing apparatuses installed in offices are sometimes used in the related art.

With regard to such an information processing apparatus, the number of multiple terminal devices having sensors with which the information processing apparatus is communicatively connectable at the same time is limited. The information processing apparatus sequentially acquires the information detected by and stored in the multiple terminal devices having the sensors by repeating communicative connection and disconnection processes that involve connecting with the terminal devices to acquire the information therefrom and then disconnecting therefrom. Accordingly, regardless of whether the information detected by the terminal devices and acquired from these terminal devices has changed or not, the information process apparatus acquires the information detected by the multiple terminal devices by communicatively connecting therewith basically under the same condition among the multiple terminal devices. Therefore, there may sometimes be a delay in the acquisition of information from a terminal device that has detected information having a changed status.

SUMMARY

Aspects of non-limiting embodiments of the present disclosure relate to suppressing a delay in the acquisition of information having a changed status, as compared with a case where the connection with a terminal device is performed without taking into consideration a change in the status of information detected by a sensor.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an information processing apparatus including a communication unit, an information acquiring unit, a setting unit, and a controller. The communication unit communicatively connects with a terminal device having a sensor. The information acquiring unit acquires information detected by the sensor from the terminal device communicatively connected via the communication unit. The setting unit sets a preferential terminal device to be preferentially connected with the communication unit. The controller performs control to connect with the preferential terminal device preferentially over a terminal device that is not a preferential terminal device within a capacity range of the communication unit.

BRIEF DESCRIPTION OF THE DRAWINGS

Exemplary embodiments of the present disclosure will be described in detail based on the following figures, wherein.

DETAILED DESCRIPTION

Figure 1:
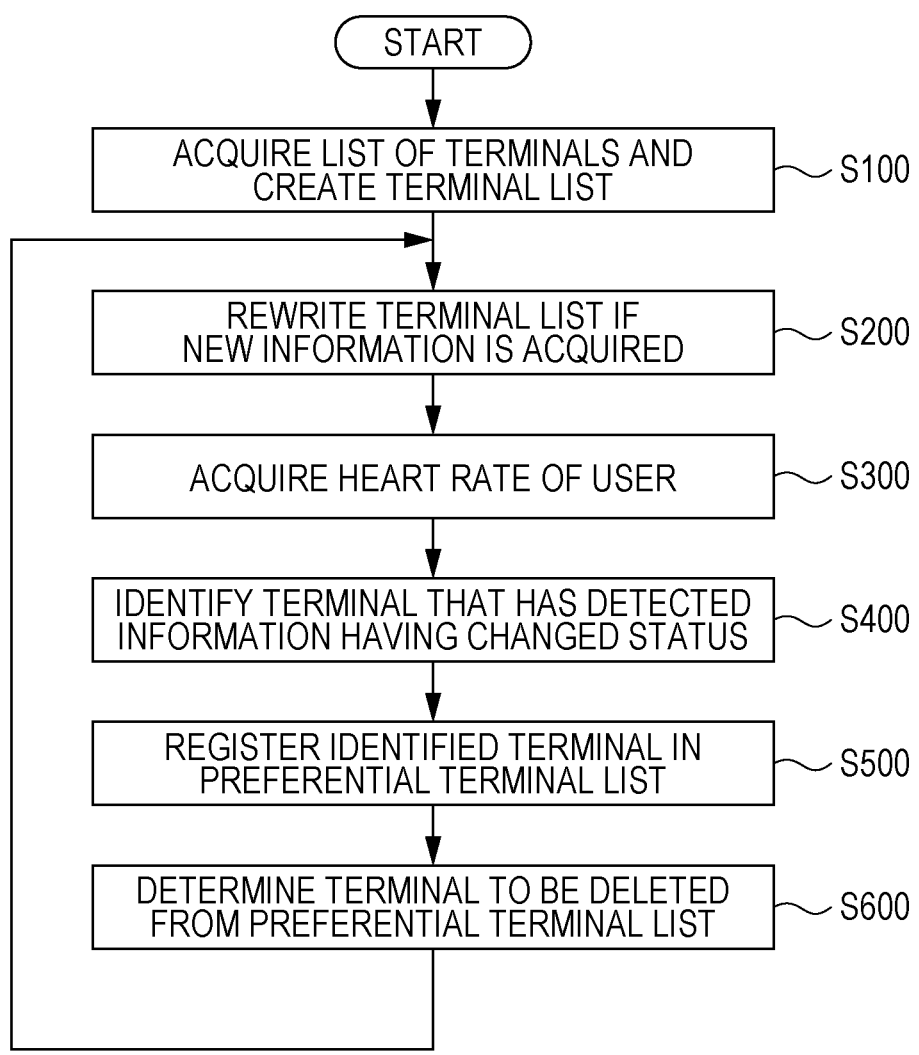
FIG. 1 is a flowchart illustrating the flow of a process performed by an information processing apparatus according to an exemplary embodiment of the present disclosure.

An information processing apparatus and an information processing program according to an exemplary embodiment of the present disclosure will now be described with reference to FIGS. 1 to 10. In the drawings, identical or equivalent components and sections are given the same reference signs. The dimensional ratios in the drawings are exaggerated for the sake of convenience and may sometimes be different from the actual ratios.

Overall Configuration

Figure 3:
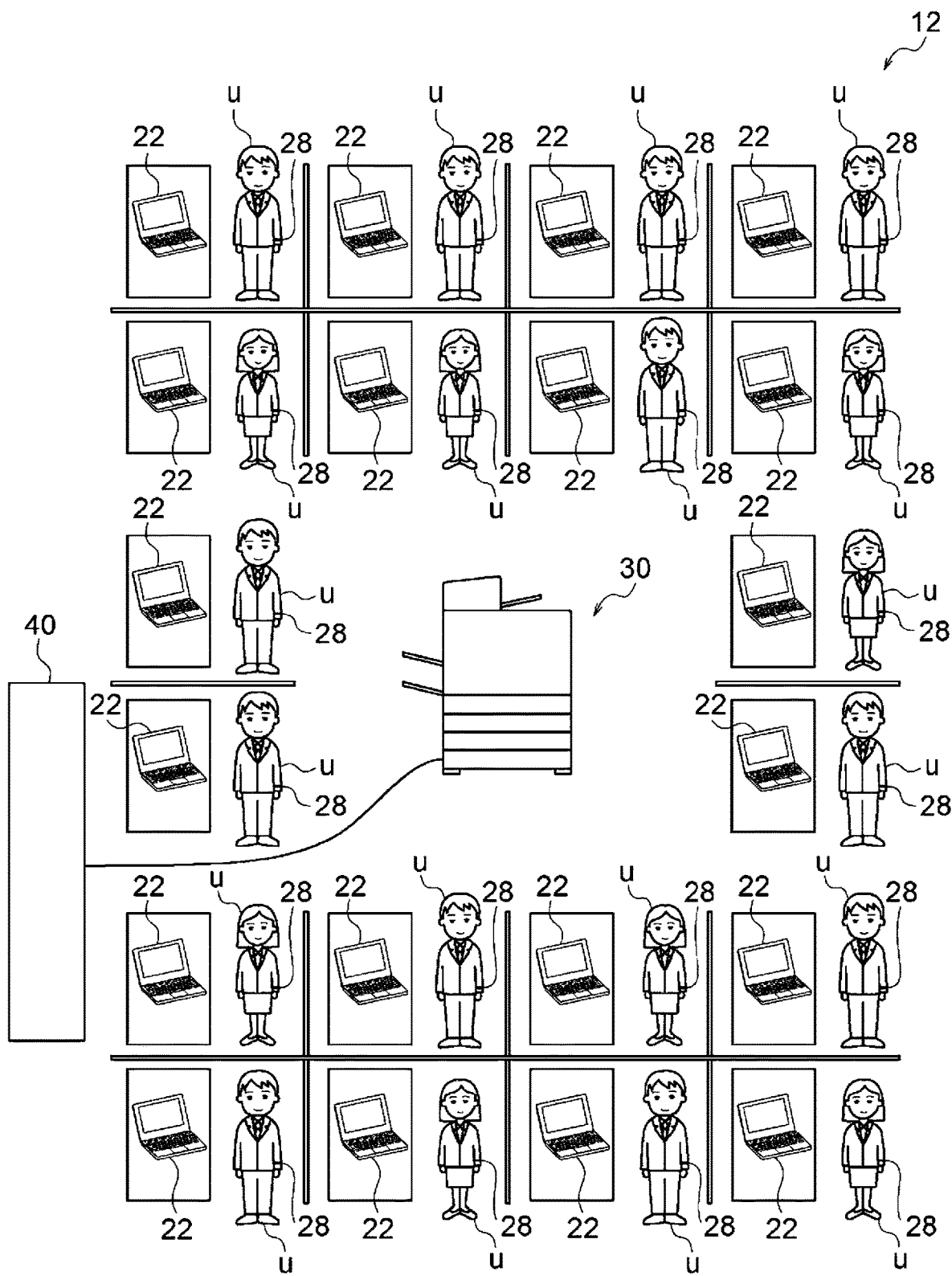
FIG. 3 schematically illustrates the configuration of a workplace in which the information processing apparatus according to the exemplary embodiment of the present disclosure is disposed.

As shown in FIG. 3, an information processing system 12 having an image processing device partially constituting an information processing apparatus according to an exemplary embodiment is at least partially provided in a workplace (referred to as "office" hereinafter). The information processing system 12 includes terminals 28 as devices having multiple sensors respectively carried by multiple users U as employees, an image processing device 30 having an information acquiring unit 301 (see FIG. 8) with which the number of terminals 28 communicatively connectable is limited, and an information processing server 40 that collects information acquired by the information acquiring unit 301 and performs analysis and management processes on the collected information.

The image processing device 30 is disposed in the middle of the office, and the seats of the users U carrying the terminals 28 having the sensors are disposed surrounding the image processing device 30. The users U individually have personal computers 22 used for requesting the image processing device 30 to perform image processing.

Terminals 28 Having Sensors

Figure 4:
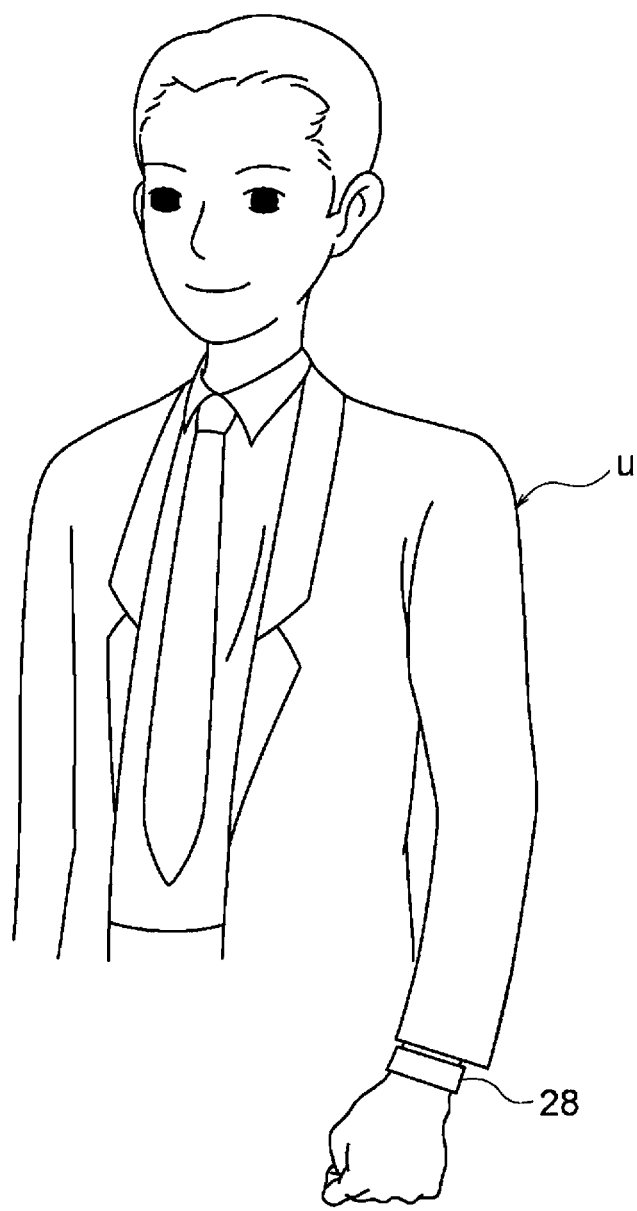
FIG. 4 illustrates the configuration of a terminal having a sensor that collects information to be processed by the information processing apparatus according to the exemplary embodiment of the present disclosure.
Figure 5:
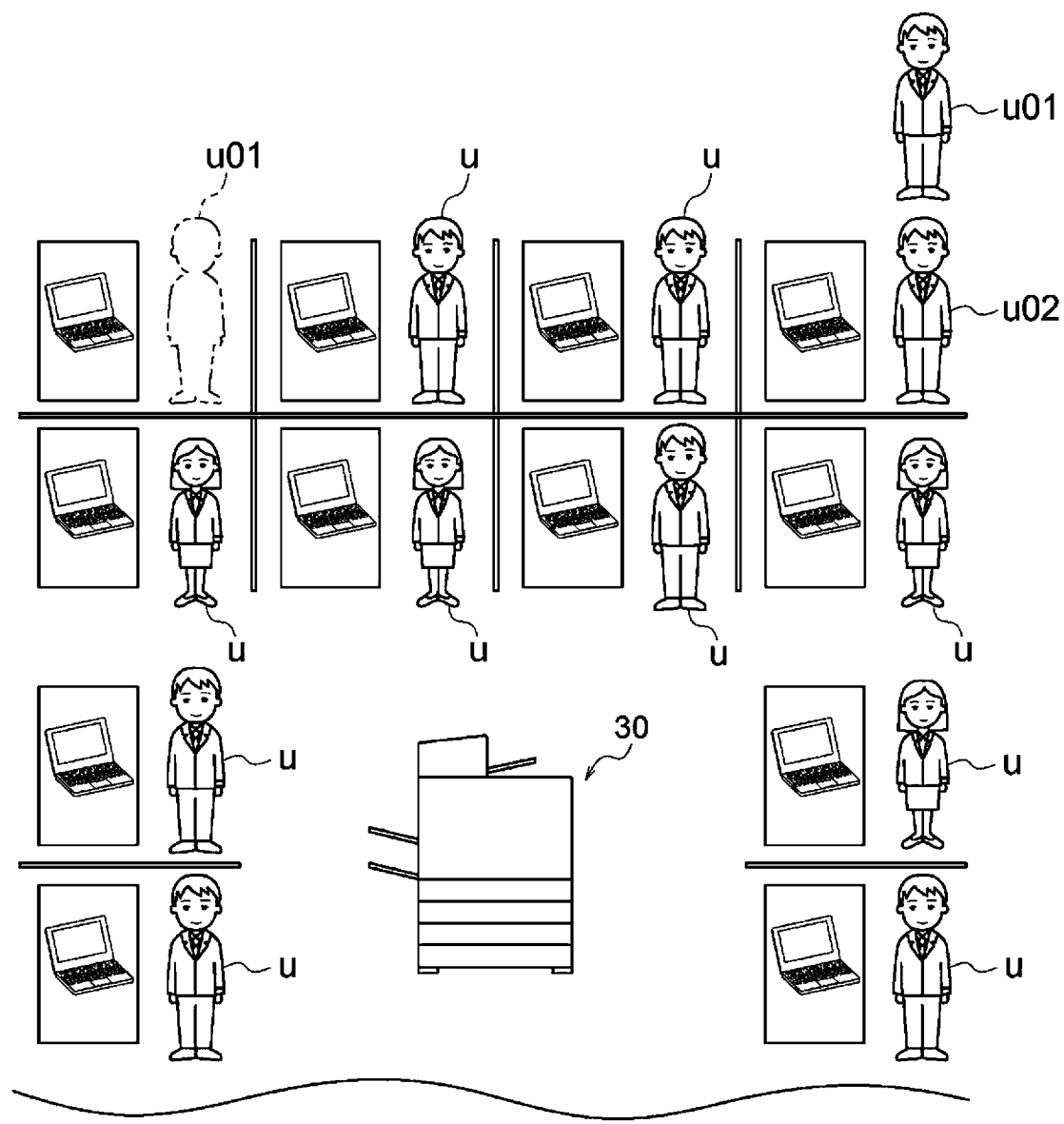
FIG. 5 is a diagram used for explaining an information-exchange user in a process performed by the information processing apparatus according to the exemplary embodiment of the present disclosure.
Figure 6:
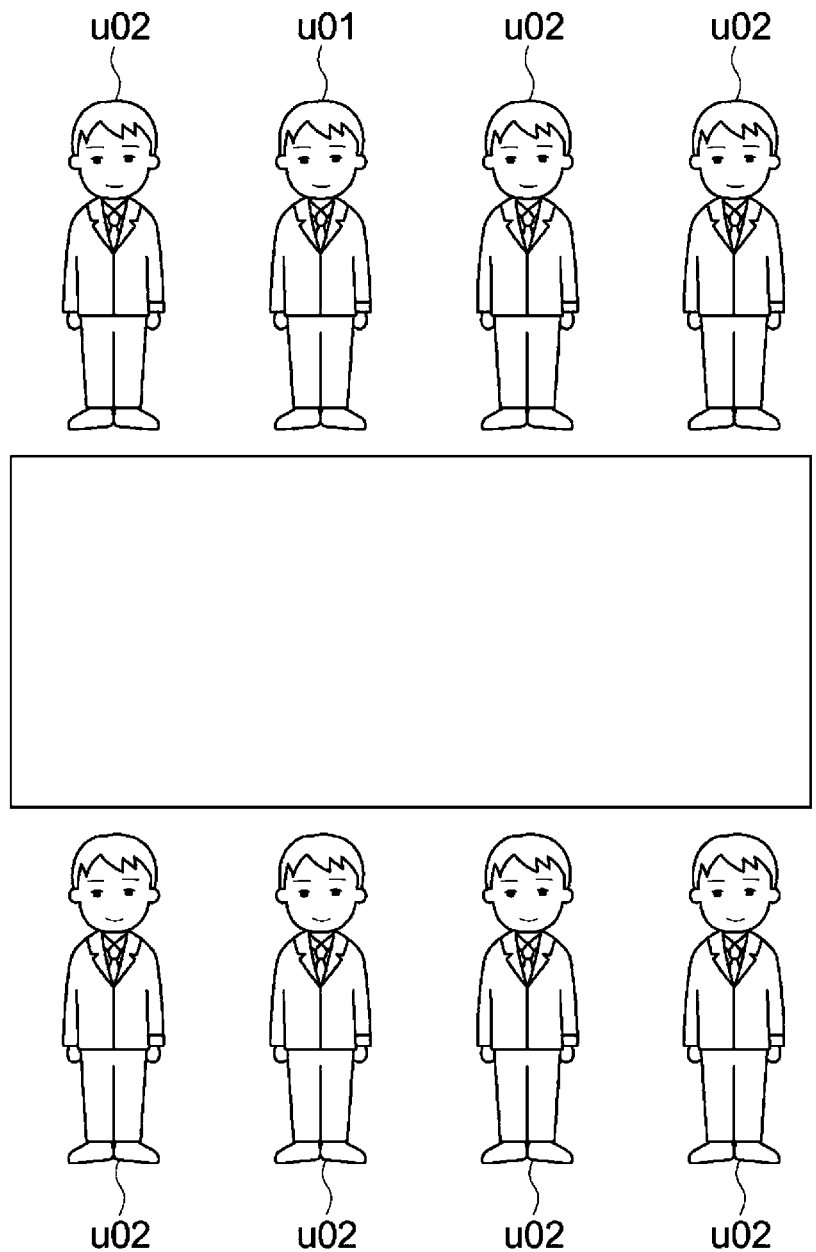
FIG. 6 is a diagram used for explaining information-exchange users in a process performed by the information processing apparatus according to the exemplary embodiment of the present disclosure.

Each terminal 28 includes a heart rate sensor as a vital sensor that detects the activity of the corresponding user U and physical information about the user's body at rest, and is worn by the user U on one of his/her wrists, as shown in FIG. 4. The terminal 28 detects the heart rate as the physical information of the user U. Specifically, the terminal 28 includes a sensor that detects various types of information and functions as an information detector that detects information by using this sensor. For example, in addition to the sensor that detects the heart rate, the terminal 28 may include multiple sensors, such as a pedometer that measures the number of steps taken and an electrocardiographic sensor that measures electrocardiographic information. Furthermore, the terminal 28 includes a storage unit that stores the information detected by the sensor and a communication interface (I/F) that exchanges information by communicatively connecting with an external device.

Image Processing Device 30

Hardware Configuration of Image Processing Device 30

Figure 7:
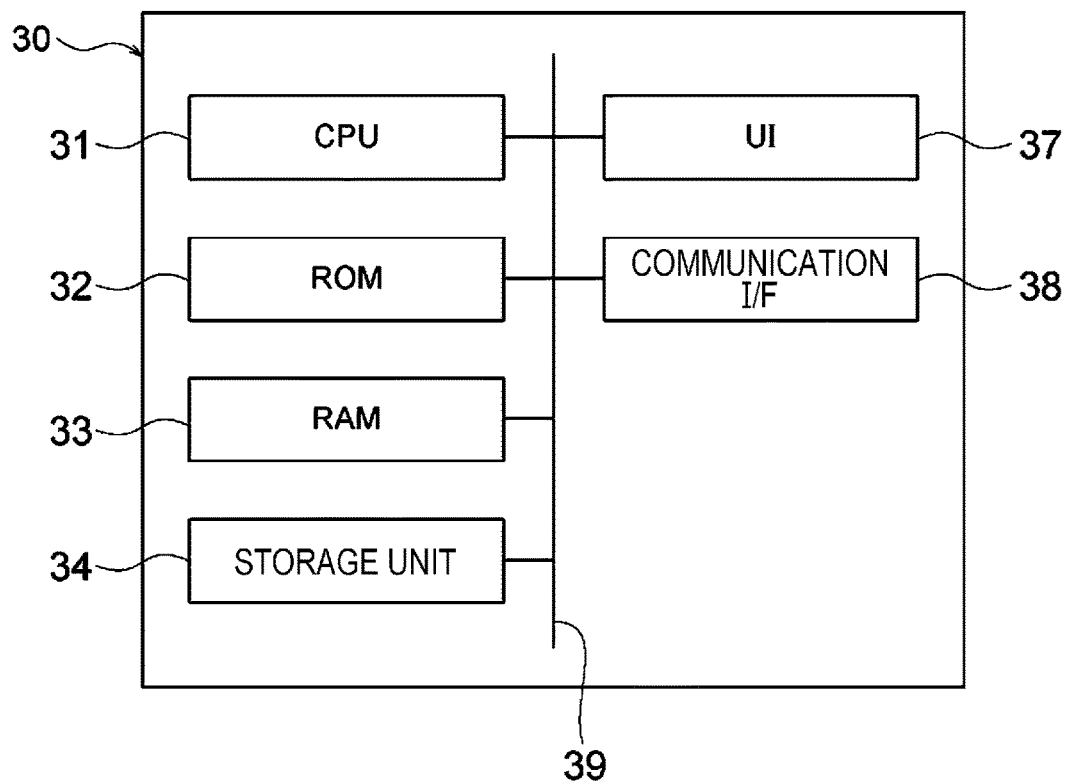
FIG. 7 is a block diagram illustrating the hardware configuration of an image processing device partially constituting the information processing apparatus according to the exemplary embodiment of the present disclosure.

As shown in FIG. 7, the hardware configuration of the image processing device 30 includes a central processing unit (CPU) 31, a read-only memory (ROM) 32, a random access memory (RAM) 33, a storage unit 34, a user interface (UI) 37, and a communication interface (I/F) 38. These components are connected with one another in a communicable manner by a bus 39.

The CPU 31 is a central processing unit that executes various types of programs and controls each component. Specifically, the CPU 31 reads a program from the ROM 32 or the storage unit 34 and executes the program by using the RAM 33 as a work area. The CPU 31 performs control of the aforementioned components and various types of calculation processes in accordance with programs stored in the ROM 32 or the storage unit 34.

The ROM 32 stores various types of programs and various types of data. The RAM 33 functions as a work area that temporarily stores a program or data. The storage unit 34 is constituted of a hard disk drive (HDD) or a solid state drive (SSD) and stores various types of programs, including an operating system, and various types of data.

The UI 37 is an interface to be used when a user U commanding the image processing device 30 to form an image onto a recording medium or a user U loading an image to the image processing device 30 uses the image processing device 30. For example, the UI 37 includes at least one of a liquid crystal display having a touchscreen that allows a user U to perform a touch operation, a voice-input reception unit that receives a voice input by a user U, and a button that may be pressed by a user U. The communication I/F 38 is an interface via which the image processing device 30 communicates with the terminals 28 and the information processing server 40. In order for the image processing device 30 to communicate with the terminals 28, for example, a standard compliant with near field communication, such as Bluetooth (registered trademark) Low Energy (BLE), is used. In order for the image processing device 30 to communicate with the information processing server 40, for example, a communication mode, including a local area network (LAN) or a wide area network (WAN) realized by a communication standard, such as Ethernet (registered trademark), and the Internet, is used.

Functional Configuration of Image Processing Device 30

Figure 8:
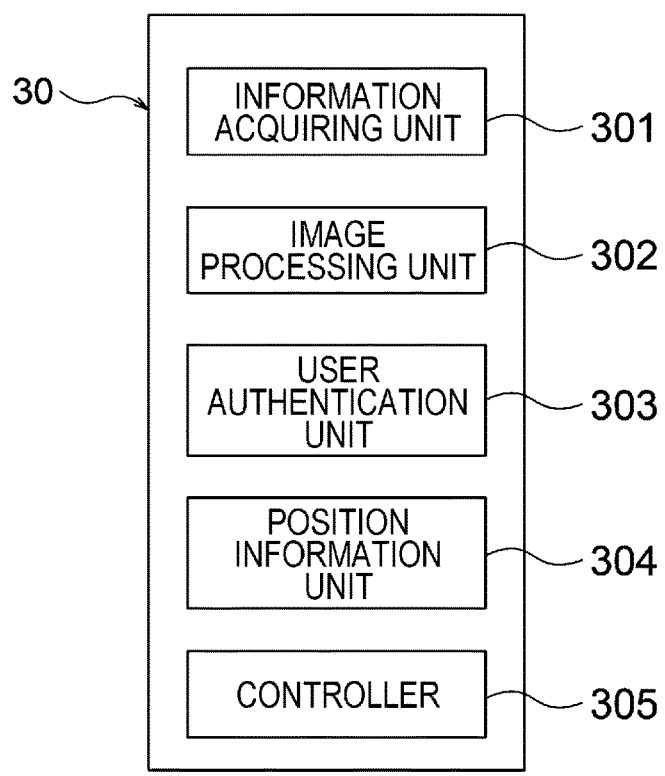
FIG. 8 is a block diagram illustrating the functional configuration of the image processing device partially constituting the information processing apparatus according to the exemplary embodiment of the present disclosure.

As shown in FIG. 8, the functional configuration of the image processing device 30 includes the information acquiring unit 301 that acquires the information detected by the sensors included in the terminals 28, an image processing unit 302, a user authentication unit 303, a position information unit 304, and a controller 305.

The information acquiring unit 301 has a function of a communication unit that communicatively connects with an external device, such as any one of the terminals 28, via the communication I/F 38, and acquires, from the communicatively-connected terminal 28, information about the heart rate detected by the sensor included in the terminal 28 and stored in the terminal 28. The heart rate is an example of information. Based on the amount of resources allocated for controlling the communicative connection, the number of external devices communicatively communicable with the information acquiring unit 301 is limited.

Based on a command from a user U, the image processing unit 302 forms image data requested for processing from the personal computer 22 of the user U onto a recording medium, changes the format of the image data, and/or processes the image data, such as forwarding the image data.

The user authentication unit 303 has, for example, authentication information about the users U, organization information about the users U, and information used for identifying the terminals 28 carried by the users U. Furthermore, the user authentication unit 303 identifies a user U who has made a processing request for forming an image onto a recording medium.

The position information unit 304 detects, for example, a BLE beacon transmitted from each terminal 28 and uses the radio output intensity of this beacon to manage the positional information of the terminal 28 and the distance information from the terminal 28.

Based on information related to preferential terminals set by a setting unit 402, to be described later, the controller 305 sequentially communicatively connects with the multiple terminals 28 and controls the information acquiring unit 301 to acquire the heart rate as information detected and stored by the heart rate sensor included in each of the terminals 28. Accordingly, the controller 305 functions as a sequence adjusting unit that adjusts the sequence in which the information acquiring unit 301 acquires the heart rates detected by the terminals 28.

Information Processing Server 40

Hardware Configuration of Information Processing Server 40

Figure 9:
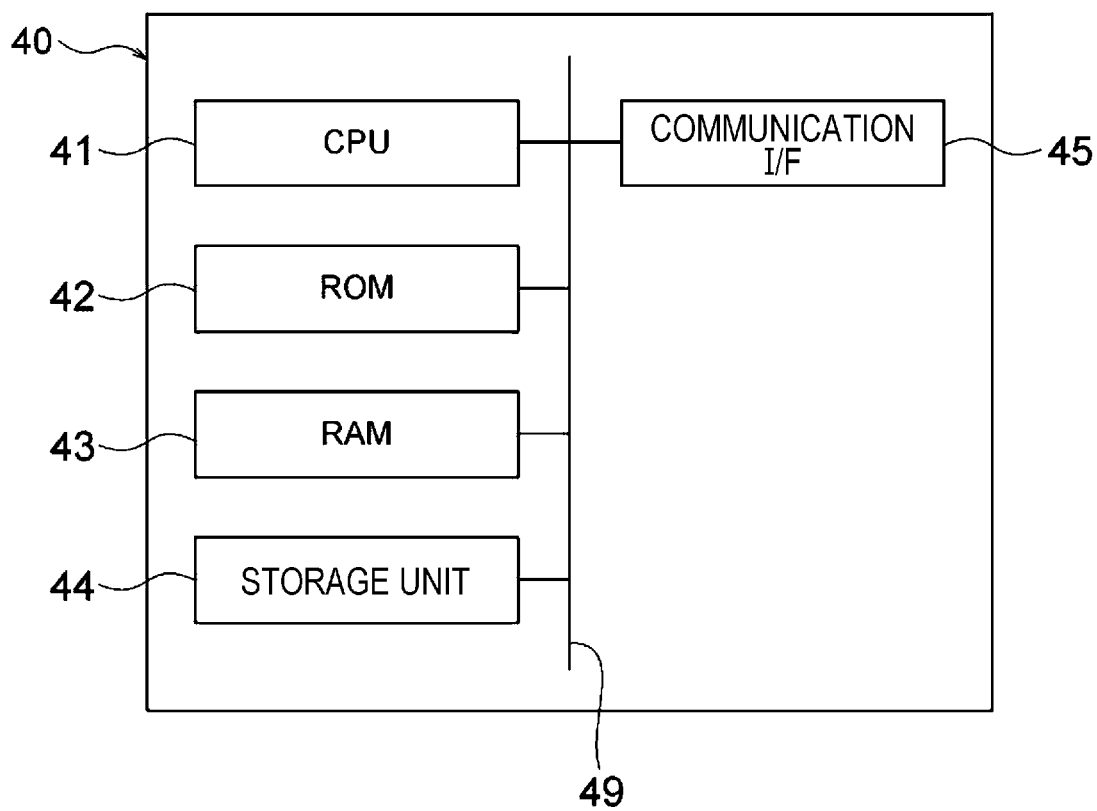
FIG. 9 is a block diagram illustrating the hardware configuration of an information processing server partially constituting the information processing apparatus according to the exemplary embodiment of the present disclosure.

As shown in FIG. 9, the hardware configuration of the information processing server 40 includes a CPU 41, a ROM 42, a RAM 43, a storage unit 44, and a communication interface 45. The components are connected with one another in a communicable manner via a bus 49. The information processing server 40 serves as a so-called server.

The CPU 41 is a central processing unit that executes various types of programs and controls each component. Specifically, the CPU 41 reads a program from the ROM 42 or the storage unit 44 and executes the program by using the RAM 43 as a work area. The CPU 41 performs control of the aforementioned components and various types of calculation processes in accordance with programs stored in the ROM 42 or the storage unit 44.

The ROM 42 stores various types of programs and various types of data. The RAM 43 functions as a work area that temporarily stores a program or data. The storage unit 44 is constituted of a hard disk drive (HDD) or a solid state drive (SSD) and stores various types of programs, including an operating system, and various types of data. The communication interface 45 is an interface for communicating with the image processing device 30 and uses a communication mode, including a local area network (LAN) or a wide area network (WAN) realized by a communication standard, such as Ethernet (registered trademark), and the Internet.

Functional Configuration of Information Processing Server 40

Figure 10:
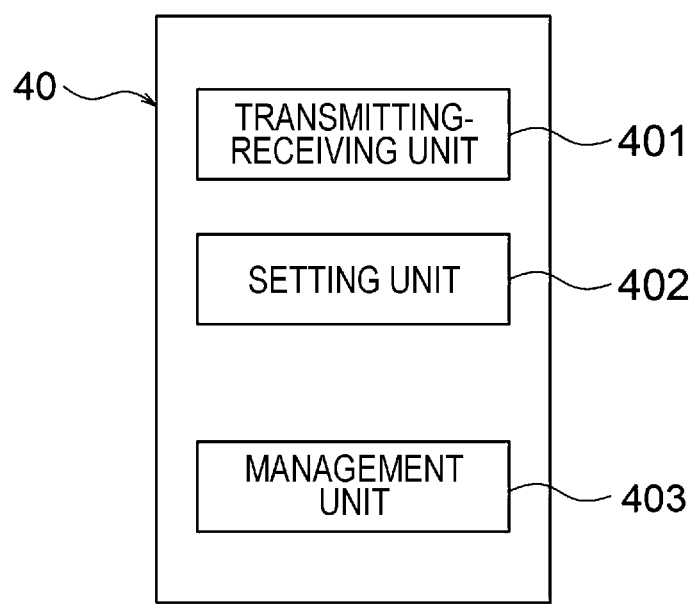
FIG. 10 is a block diagram illustrating the functional configuration of the information processing server partially constituting the information processing apparatus according to the exemplary embodiment of the present disclosure.

As shown in FIG. 10, the functional configuration of the information processing server 40 includes a transmitting-receiving unit 401, a setting unit 402, and a management unit 403.

The transmitting-receiving unit 401 receives, via the information acquiring unit 301 of the image processing device 30, the heart rate of each user U detected by the heart rate sensor included in the corresponding terminal 28. Furthermore, the transmitting-receiving unit 401 transmits control information with respect to the information acquiring unit 301 to the controller 305 of the image processing device 30.

Based on a command from the management unit 403 that manages data, such as the received heart rate of each user U, the setting unit 402 sets terminals 28 from which the information acquiring unit 301 of the image processing device 30 preferentially acquires heart rates. Then, the setting unit 402 sets a terminal list having a preferential terminal list and a normal terminal list. In the preferential terminal list, terminals 28 set as preferential terminals from which heart rates are preferentially acquired are registered, and the number of registerable terminals is limited. In the normal terminal list, terminals 28 not registered in the preferential terminal list are registered. This terminal list contains terminal identification information allocated to each terminal 28.

The management unit 403 manages the data of the received heart rate of each user U. If a steady heart rate value of the user U is to be calculated by accumulating the data of the acquired heart rate of the user U or if the acquired heart rate value deviates from a steady value by a predetermined value, the management unit 403 determines that there is a possibility of a physical abnormality or detects a displacement pattern of a prediction value for a physical abnormality, so as to manage the physical condition of the user U. Furthermore, based on the workload, the type of work, and the processing state of work of the user U, the management unit 403 may determine that information about the physical condition of the user U is to be preferentially acquired. If there is a large workload, the physical condition may possibly deteriorate due to fatigue. In that case, it may be determined that the information is to be preferentially acquired. If it is determined from the type of work or the processing state of work that the user U is in a state of extreme tension, it is determined that the information related to the physical condition is to be preferentially acquired. When it is determined that the information is to be acquired preferentially over other users U in this manner, the setting unit 402 is commanded to preferentially acquire, from the terminal 28 carried by this user U, the data of the heart rate measured by the sensor included in the terminal 28.

As described above, an information management system that manages the information detected by the sensor included in each terminal 28 is constituted by including the information acquiring unit 301 and the controller 305 provided in the image processing device 30 and the setting unit 402 and the management unit 403 provided in the information processing server 40.

A specific configuration of the information management system will be described below together with the operation thereof.

Operation

Next, the operation of the information management system will be described with reference to flowcharts shown in FIGS. 1 and 2. The information management system has a function of managing the health condition of each user U. In detail, under a condition in which the number of terminals 28 communicatively connectable with the information acquiring unit 301 is limited, the information management system collects and manages data measured by each terminal 28 while suppressing a delay in the acquisition of the heart rate from a terminal 28 that has detected information having a changed status.

The following description relates to a process performed in the setting unit 402 of the information processing server 40 for creating the terminal list having the preferential terminal list and the normal terminal list in which terminals 28 not registered in the preferential terminal list are registered. As mentioned above, the preferential terminal list is a list in which terminals 28 from which heart rates are preferentially acquired are registered and the number of registerable terminals is limited.

A method of determining the number of preferentially-connected terminals and the number of normally-connected terminals to be registered in the terminal list will be described below. For example, assuming that the resources that the controller 305 of the image processing device 30 is communicatively connectable with multiple terminals 28 are "20", a resource for communicatively connecting with the normally-connected terminals is "1" and resources for communicatively connecting with the preferentially-connected terminals are "3".

In an initial state where there are no terminals to be preferentially connected, the normal terminal list has normally-connected terminals indicated therein. Of the indicated terminals, the controller 305 connects with terminals 28 while the upper limit is "20", acquires information from the terminals 28, and disconnects therefrom after acquiring the information. This process is sequentially performed while the upper limit of "20" corresponding to the number of connections with the terminals 28. When a terminal to be preferentially connected is identified, the terminal is listed in the preferential terminal list, and the resource "3" of the upper limit resource "20" is allocated to the preferentially-connected terminal. As a result, the resources allocated to the terminals indicated in the normal terminal list for connection become "17". In this case, the setting unit 402 of the information processing server 40 creates a terminal list containing identification information of the single terminal 28 to be preferentially connected and the number of normally-connected terminals "17", and transmits the terminal list to the image processing device 30. The method described here is an example of control for the number of connections, and another method may be employed. For example, the setting unit 402 of the information processing server 40 may create a list having information in which a terminal 28 from which information is to be preferentially acquired in the terminal list is rewritten from "normal" to "preferential", and may transmit the list to the image processing device 30. As another alternative, the setting unit 402 of the information processing server 40 may create a terminal list of only terminals 28 from which information is to be preferentially acquired, and may transmit the terminal list to the image processing device 30. As another alternative, the setting unit 402 of the information processing server 40 may simply notify the image processing device 30 of the identification information of a terminal 28 from which information is to be preferentially acquired.

Next, a process in which the information acquiring unit 301 acquires the heart rate detected by each terminal 28 based on the terminal list acquired from the information processing server 40 will be described.

Process for Creating Terminal List

FIG. 1 is a flowchart of a process performed by the setting unit 402 for creating the terminal list.

In step S100 shown in FIG. 1, in a state where a terminal list is not created, the setting unit 402 of the information processing server 40 acquires, from the user authentication unit 303 of the image processing device 30, a list that contains identification information of the terminals 28 carried by the users U. Furthermore, the setting unit 402 creates a terminal list from the acquired list. At this point, all of the terminals 28 are registered in the normal terminal list. With regard to the terminal list, a list containing identification information of the terminals 28 respectively carried by the multiple users U as employees in the office in which the image processing device 30 is disposed may be created in advance and be registered in the information processing server 40.

In step S200, if the setting unit 402 has acquired new information with respect to rewriting of the terminal list, the setting unit 402 rewrites the terminal list. If new information has not been acquired, the process proceeds directly to step S300.

In step S300, the setting unit 402 acquires the heart rate detected by the sensor included in each terminal 28 via the information acquiring unit 301 of the image processing device 30. In detail, the information acquiring unit 301 acquires the heart rate of the corresponding user U detected by the sensor included in the terminal 28. Then, the setting unit 402 acquires, via the information acquiring unit 301, the heart rate of each user U acquired by the information acquiring unit 301. The process performed by the information acquiring unit 301 for acquiring the heart rate of each user U detected by the sensor included in the corresponding terminal 28 will be described later.

In step S400, the setting unit 402 identifies a terminal 28 that has detected information indicating a change considered to be an abnormal condition or a sign of an abnormality. Moreover, the setting unit 402 identifies a terminal 28 from which information is to be preferentially acquired based on information other than the data acquired via the information acquiring unit 301 of the image processing device 30, such as the workload, the type of work, or the processing state of work. In other words, the setting unit 402 identifies terminals 28 of interest for managing the health of the users U.

In detail, the setting unit 402 identifies a terminal 28 in accordance with first to fourth conditions described below.

According to the first condition, the setting unit 402 identifies a terminal 28 that has detected a heart rate higher than or equal to a predetermined threshold value. Specifically, the setting unit 402 identifies a terminal 28 carried by a user U who may possibly have an adverse effect on the health condition.

According to the second condition, the setting unit 402 identifies a terminal 28 that has detected a heart rate that has changed by a predetermined threshold value or more within a predetermined period. Specifically, the setting unit 402 identifies a terminal 28 carried by a user U who may possibly have an adverse effect on the health condition.

According to a third condition, the setting unit 402 identifies a terminal 28 carried by a user U (referred to as "preferential user U01" hereinafter) whose processing-request frequency indicating the number of times the user U has made a processing request to the image processing device 30 within a predetermined period has changed by a predetermined threshold value or more. Specifically, the setting unit 402 identifies a terminal 28 carried by a user U having more workload than usual, presumable as performing a job different from usual, or determinable as being in a state of tension due to work.

The following is a detailed description of how a preferential user U01 is set.

First, the user authentication unit 303 of the image processing device 30 identifies a user U who has made a processing request for, for example, printing, scanning, or image conversion to an image processing function included in the image processing device 30. The setting unit 402 acquires the identified user U from the user authentication unit 303 and acquires information related to the processing-request frequency from the image processing unit 302.

Furthermore, the setting unit 402 acquires a reference processing-request frequency stored in the user authentication unit 303 and set for each user U from the user authentication unit 303. A reference processing-request frequency set for each user U is a processing-request frequency calculated based on the number of times the user U has made a processing request to the image processing device 30 within a predetermined period in the past, or a predetermined average processing-request frequency.

Then, the setting unit 402 sets a user U whose processing-request frequency has changed by a predetermined threshold value or more relative to the reference processing-request frequency as a preferential user U01. In other words, the setting unit 402 sets a user U whose processing-request frequency differs from the reference processing-request frequency by the predetermined threshold value or more as a preferential user U01.

The reason that the user U whose processing-request frequency has changed by the predetermined threshold value or more is set as a preferential user U01 and that the terminal 28 carried by this preferential user U01 is identified is because it is presumed from the change in the processing-request frequency by the predetermined threshold value or more that the preferential user U01 may possibly be in a state of tension or may possibly have an adverse effect on the health condition due to, for example, an increase in workload or an urgent job. Accordingly, the setting unit 402 identifies the terminal 28 carried by the user U from which data is to be preferentially acquired.

According to the fourth condition, the setting unit 402 identifies a terminal 28 carried by a user U (referred to as "information-exchange user U02" hereinafter) who is exchanging information with the preferential user U01.

The following is a detailed description of how an information-exchange user U02 is set.

First, the setting unit 402 refers to meeting information of the preferential user U01 from a schedule manager (not shown) based on the user authentication unit 303, so as to acquire meeting information and attendance information for the current time (i.e., today). If there is a meeting, the setting unit 402 sets each of users U participating in the meeting as an information-exchange user U02 (see FIG. 6). The schedule manager (not shown) may be a service provided by the information processing server 40.

Furthermore, the setting unit 402 acquires the travel destination of the terminal 28 carried by the preferential user U01 and information about each user U carrying a terminal 28 located at the travel destination from the position information unit 304. The setting unit 402 sets each user U carrying a terminal 28 located at the travel destination as an information-exchange user U02 (see FIG. 5). Positional information of the users U01 and U02 may be identified from distance information between the users U01 and U02 acquired by the position information unit 304 of the image processing device 30. Alternatively, a position sensor set in the office may detect the positions of the terminals 28 carried by the users U01 and U02, and the positional information may be acquired from this position sensor.

The reason that each user U exchanging information with the preferential user U01 is set as an information-exchange user U02 and that the terminal 28 carried by each information-exchange user U02 is identified is because the information-exchange user U02 exchanging information with the preferential user U01 whose processing-request frequency has changed by the predetermined threshold value or more may also possibly have an adverse effect on the health condition. For example, due to a heavy workload, the preferential user U01 is identified as a user U whose processing-request frequency has changed by the predetermined threshold value or more relative to the reference processing-request frequency. Then, an information-exchange user U02 exchanging information with the busy preferential user U01 is also identified as being busy. This is because the busy information-exchange user U02 may also possibly have an adverse effect on the health condition due to being in a state of tension or fatigue. Accordingly, the setting unit 402 identifies terminals 28 carried by users U who may possibly have an adverse effect on the health condition.

Subsequently, in step S500, the setting unit 402 confirms that each terminal 28 identified in step S400 is to be registered in the terminal list as a terminal from which information is to be preferentially acquired, and registers the terminal 28 in the preferential terminal list.

Then, in step S600, of the terminals 28 registered in the preferential terminal list, the setting unit 402 checks whether there is any terminal 28 to be moved to the normal terminal list. If it is confirmed that the normal condition is regained by analyzing information acquired from a terminal 28, this terminal 28 is deleted from the preferential terminal list and is additionally registered in the normal terminal list. In detail, the setting unit 402 determines to delete, from the preferential terminal list, a terminal 28 that has detected a heart rate that has not greatly changed within a predetermined period (i.e., threshold-value period). The expression "a terminal 28 that has detected a heart rate that has not greatly changed" refers to a sensor, which has not detected a noteworthy heart rate, as a terminal 28 of interest for managing the health of the corresponding user U.

The process then proceeds to step S200. With regard to the terminal list containing identification information of terminals from which data is to be preferentially acquired and identification information of terminals from which data is to be normally acquired, the identification information of the terminals 28 from which data is to be preferentially acquired is registered in the preferential terminal list. If there is a terminal 28 that is to be returned to the normal terminal list from the preferential terminal list, the terminal list is rewritten such that the terminal 28 is deleted from the preferential terminal list and is added to the normal terminal list. The above-described process is then repeated.

Process for Acquiring Heart Rate Detected by Terminal 28

Figure 2:
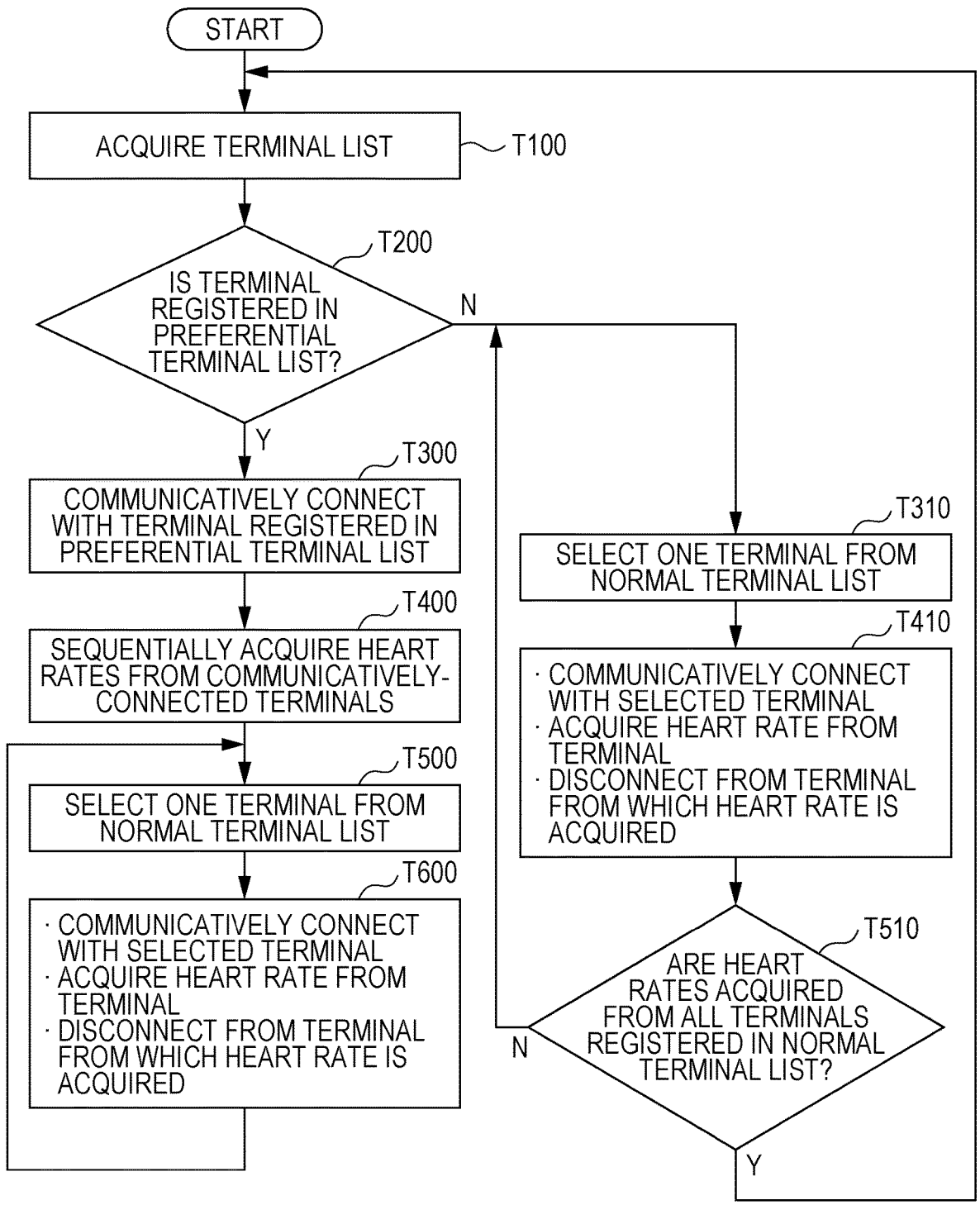
FIG. 2 is a flowchart illustrating the flow of a process performed by the information processing apparatus according to the exemplary embodiment of the present disclosure.

FIG. 2 is a flowchart illustrating the flow of a process performed by the information acquiring unit 301 for acquiring the heart rate detected by the sensor included in each terminal 28.

First, in step T100, the controller 305 of the image processing device 30 acquires the terminal list from the setting unit 402 of the information processing server 40. In detail, the controller 305 acquires, from the setting unit 402, the terminal list in step S200 shown in the flowchart in FIG. 1.

Next, in step T200, the controller 305 determines whether or not a terminal 28 is registered in the preferential terminal list within the terminal list. If a terminal 28 is registered in the preferential terminal list, the process proceeds to step T300. If a terminal 28 is not registered in the preferential terminal list, the process proceeds to step T310.

In step T300, the controller 305 allows the information acquiring unit 301 and the terminal 28 registered in the preferential terminal list to communicatively connect with each other. As mentioned above, there is an upper limit to the resources that the information acquiring unit 301 is communicatively connectable with the terminals 28, and the connection is started from the terminals indicated in the preferential terminal list. In some cases, the connection is started sequentially with the terminals indicated in the preferential terminal list, and when the upper limit of the resources is reached, the connection with subsequent terminals 28 may become impossible. Accordingly, in this exemplary embodiment, the information acquiring unit 301 also has a function of a communication unit that communicatively connects with the terminals 28.

In step T400, the information acquiring unit 301 sequentially acquires, from the communicatively-connected terminals 28, the heart rates detected by the sensors included in the terminals 28. Specifically, the information acquiring unit 301 sequentially acquires, from each of the connected terminals 28, information about the heart rate detected by each terminal 28 registered in the preferential terminal list. Then, the information acquiring unit 301 saves the information about the heart rate for each terminal 28.

In step T500, in a state where the communicative connection between the information acquiring unit 301 and each terminal 28 indicated in the preferential terminal list is maintained, the controller 305 selects one of the terminals 28 from the normal terminal list.

Then, in step T600, in a state where the communicative connection between the information acquiring unit 301 and each terminal 28 registered in the preferential terminal list is maintained, the controller 305 allows the information acquiring unit 301 and the terminal 28 selected in step T500 to communicatively connect with each other. Specifically, after the connection with all of the terminals 28 indicated in the preferential terminal list is completed, the connection with the terminals 28 indicated in the normal terminal list is sequentially performed within the range of the remaining resources. Then, the information acquiring unit 301 acquires the heart rate detected by each of these terminals 28. Moreover, the information acquiring unit 301 saves the heart rate from each terminal 28. When the information acquiring unit 301 acquires the heart rate detected by each terminal 28, the controller 305 disconnects the communicative connection between the information acquiring unit 301 and the terminal 28. Subsequently, a communicative connection with the next terminal 28 indicated in the normal terminal list is performed. This is sequentially repeated for the terminals 28 indicated in the normal terminal list.

If a terminal 28 is not registered in the preferential terminal list in step T200, the process proceeds to step T310 where the controller 305 selects a number of terminals 28 indicated in the normal terminal list up to the upper limit of the resources.

In step T410, the controller 305 allows the information acquiring unit 301 and the terminals 28 selected in step T310 to communicatively connect with each other, and the information acquiring unit 301 acquires the heart rate detected by each of these terminals 28. When the heart rate detected by the terminal 28 is acquired, the controller 305 disconnects the communicative connection between the information acquiring unit 301 and the terminal 28.

In a case where the heart rates detected by the terminals 28 registered in the normal terminal list are acquired in step T510, the process proceeds to step T100 to repeat the above-described process.

If the heart rates detected by the terminals 28 registered in the normal terminal list are not acquired in step T510, the process proceeds to step T310 to repeat the above-described process. In step T310, a terminal 28 not selected from the terminals 28 registered in the normal terminal list is selected.

Miscellaneous

The heart rate acquired by the information acquiring unit 301 is transmitted to the information processing server 40. Then, the transmitting-receiving unit 401 of the information processing server 40 provides a notification about the heart-rate information to the user U who may possibly have an adverse effect on the health condition and to a health manager by using an electronic mail.

Although a specific exemplary embodiment has been described above in detail, the present disclosure is not limited to the above exemplary embodiment. It is obvious to a person skilled in the art that various exemplary embodiments are possible within the scope of the disclosure. For example, in the above exemplary embodiment, the terminals 28 are carried by the users U and detect the heart rates of the users U as information. Alternatively, the sensors may each detect environment-related information, such as the temperature, humidity, or noise in a predetermined space in the workplace. In this case, if there is a noteworthy change in the detected information related to the temperature, humidity, or noise, a delay in the acquisition of the information detected by the sensor may be suppressed.

In the above exemplary embodiment, the setting unit 402 sets the preferential terminal list such that a heart rate detected by a terminal 28 that has detected a heart rate higher than or equal to the predetermined threshold value is preferentially acquired. Alternatively, the setting unit 402 may set the preferential terminal list such that a heart rate detected by a sensor that has detected a heart rate lower than or equal to a predetermined threshold value is preferentially acquired.

Furthermore, in the above exemplary embodiment, the setting unit 402 sets the preferential terminal list such that a heart rate detected by a terminal 28 that has detected a heart rate that has changed by the predetermined threshold value or more is preferentially acquired. Alternatively, the setting unit 402 may set the preferential terminal list such that a heart rate detected by a sensor that has detected that the number of times the heart rate has changed by the predetermined threshold value or more is more than or equal to a threshold value is preferentially acquired.

Furthermore, in the above exemplary embodiment, the preferential terminal list indicating terminals to be preferentially connected and the normal terminal list indicating terminals that do not have to be preferentially connected are described. Alternatively, the terminal list may be created such that it contains priority levels for connection together with the identification information of the terminals. For example, the priority levels for the terminals to be preferentially connected may be allocated thereto starting from the first priority level, and a value that does not overlap with the number of terminals to be preferentially connected may be allocated to all of the terminals to be normally connected, such as allocating a priority level of "100" thereto.

Furthermore, in the above exemplary embodiment, the image processing device 30 is used to describe an image processing device. Alternatively, for example, a scanner or a facsimile device may be used, so long as the device is configured to process an image.

Furthermore, in the above exemplary embodiment, the setting unit 402 sets the preferential terminal list based on a change in the degree of a processing request made to the image processing device 30 by a user U. Alternatively, the preferential terminal list may be set based on the degree by which the user U who has requested the image processing device 30 to process an image approaches the image processing device 30. In this case, for example, the request made by the approaching user U for processing an image may be prioritized.

Furthermore, in the above exemplary embodiment, the information management system is constituted of the image processing device 30 and the information processing server 40 connected thereto via a network. Alternatively, the image processing device 30 and the information processing server 40 may be included in a single apparatus.

Furthermore, although not specified in the above exemplary embodiment, a user U carrying a terminal 28 having a sensor located at a distance substantially equal to the distance between the terminal 28 of the preferential user U01 and the image processing device 30 may be regarded as an information-exchange user U02.

Furthermore, although not specified in the above exemplary embodiment, a user U who is carrying a terminal 28 having a sensor located at a distance substantially equal to the distance between the terminal 28 of the preferential user U01 and the image processing device 30 and who belongs to the same organization as the preferential user U01 may be regarded as an information-exchange user U02.

Furthermore, although not specified in the above exemplary embodiment, if a user U moves outside the communication range of the information acquiring unit 301 of a first image processing device 30, the information acquiring unit 301 of a second image processing device 30 may acquire the heart rate detected by the terminal 28 carried by the user U and may transmit the heart rate to the first image processing device 30.

Furthermore, although not specified in the above exemplary embodiment, a preferential terminal may be set such that a heart rate detected by a sensor of a terminal 28 carried by a user U whose total labor time is longer than or equal to a threshold value is preferentially acquired.

In the above exemplary embodiments, the information processing executed by the CPU 31 or 41 reading software (program) may be executed by various types of processors other than a CPU. In this case, examples of such processors include a programmable logic device (PLD) whose circuit configuration is changeable after being manufactured, such as a field-programmable gate array (FPGA), and a dedicated electrical circuit as a processor having a circuit configuration specially designed for executing specific processing, such as an application specific integrated circuit (ASIC). The information processing may be executed in one of these various types of processors, or may be executed using a combination of two or more processors of the same type or of different types (e.g., a combination of multiple FPGAs or a combination of a CPU and an FPGA). More specifically, the hardware structure of these various types of processors is an electrical circuit having a combination of circuit elements, such as semiconductor elements.

Furthermore, in the above exemplary embodiments, the information processing program is described as being preliminarily stored (installed) in the ROM 32 or 42 or in the storage unit 34 or 44. Alternatively, the program may be provided by being stored in a storage medium, such as a compact disc read-only memory (CD-ROM), a digital versatile disc read-only memory (DVD-ROM), or a universal serial bus (USB) memory. As another alternative, the program may be downloaded from an external device via a network.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing apparatus comprising:
a communication interface that communicatively connects with a terminal device having a sensor;
a processor configured to function as:
an information acquiring unit that acquires information detected by the sensor from the terminal device communicatively connected via the communication interface; and
a setting unit that sets a preferential terminal device to be preferentially connected with the communication interface; and
a controller that performs control to connect with the preferential terminal device preferentially over a terminal device that is not a preferential terminal device within a capacity range of the communication interface,
wherein the preferential terminal device is a terminal device corresponding to a user who has made a change in a degree of a request for processing to the information processing apparatus above a threshold amount,
wherein the change in the degree of the request indicates that a processing-request frequency per unit time has changed by a threshold value or more, and
wherein the preferential terminal device is a first preferential terminal device, and, as a second preferential terminal device to be preferentially connected with the communication interface, the setting unit sets a terminal device carried by an information-exchange user who is exchanging information with a preferential user carrying the first preferential terminal device.

2. The information processing apparatus according to claim 1,
wherein the controller performs the control to connect with a normal terminal device that is not a preferential terminal device within a remaining capacity range of the communication interface connected with the preferential terminal device.

3. The information processing apparatus according to claim 2,
wherein the setting unit sets the preferential terminal device as the normal terminal device when the information does not have to be preferentially acquired from the preferential terminal device.

4. The information processing apparatus according to claim 2,
wherein the controller performs a disconnection process when the information is acquired from the connected normal terminal device.

5. The information processing apparatus according to claim 1,
wherein the preferential terminal device is a terminal device that has detected information with a predetermined threshold value or higher.

6. The information processing apparatus according to claim 1,
wherein the setting unit acquires information for identifying the preferential terminal device.

7. A non-transitory computer readable medium storing a program causing a computer to execute a process, the process comprising:
communicatively connecting with a terminal device having a sensor;
acquiring information detected by the sensor from the communicatively-connected terminal device;
setting a preferential terminal device to be preferentially connected; and
performing control to connect with the preferential terminal device preferentially over a terminal device that is not a preferential terminal device within a communication capacity range,
wherein the preferential terminal device is a terminal device corresponding to a user who has made a change in a degree of a request for processing above a threshold amount, wherein the change in the degree of the request indicates that a processing-request frequency per unit time has changed by a threshold value or more, and wherein the preferential terminal device is a first preferential terminal device, and, as a second preferential terminal device to be preferentially connected with the communication interface, the setting includes setting a terminal device carried by an information-exchange user who is exchanging information with a preferential user carrying the first preferential terminal device.

8. An information processing apparatus comprising:

communication means for communicatively connecting with a terminal device having a sensor;

information acquiring means for acquiring information detected by the sensor from the terminal device communicatively connected via the communication means;

setting means for setting a preferential terminal device to be preferentially connected with the communication means; and control means for performing control to connect with the preferential terminal device preferentially over a terminal device that is not a preferential terminal device within a capacity range of the communication means, wherein the preferential terminal device is a terminal device corresponding to a user who has made a change in a degree of a request for processing above a threshold amount, wherein the change in the degree of the request indicates that a processing-request frequency per unit time has changed by a threshold value or more, and wherein the preferential terminal device is a first preferential terminal device, and, as a second preferential terminal device to be preferentially connected with the communication means, the setting means sets a terminal device carried by an information-exchange user who is exchanging information with a preferential user carrying the first preferential terminal device.

* * * * *